United States Patent [19]

Boarini et al.

[11] 4,411,654
[45] Oct. 25, 1983

[54] PEELABLE CATHETER WITH SECURING RING AND SUTURE SLEEVE

[75] Inventors: Edward J. Boarini, Cary; Joseph W. Jonker, Round Lake, both of Ill.

[73] Assignee: Baxter Travenol Laboratories, Inc., Deerfield, Ill.

[21] Appl. No.: 259,280

[22] Filed: Apr. 30, 1981

[51] Int. Cl.³ .......................................... A61M 25/00
[52] U.S. Cl. ..................................... 604/165; 604/161
[58] Field of Search ............ 128/214.4, 221, 347-350, 128/DIG. 16; 604/158-170

[56] References Cited

U.S. PATENT DOCUMENTS

| | | | |
|---|---|---|---|
| 2,735,432 | 2/1956 | Hudson | 128/348 |
| 3,055,361 | 9/1962 | Ballard | 128/214 |
| 3,097,646 | 7/1963 | Scislowicz | 128/214 |
| 3,185,152 | 5/1965 | Ring | 128/214 |
| 3,219,036 | 11/1965 | Stafford | 128/214 |
| 3,359,978 | 12/1967 | Smith, Jr. | 128/214.4 |
| 3,382,872 | 5/1968 | Rubin | 128/214.4 |
| 3,500,828 | 3/1970 | Podhora | 128/214.4 |
| 3,515,137 | 6/1970 | Santomieri | 128/214.4 |
| 3,537,451 | 10/1966 | Beck et al. | 128/214.4 |
| 3,550,591 | 12/1970 | MacGregor | 128/214.4 |
| 3,568,660 | 3/1971 | Crites et al. | 128/419 P |
| 3,570,485 | 3/1971 | Reilly | 128/214.4 |
| 3,589,361 | 6/1968 | Loper et al. | 128/214.4 |
| 3,677,243 | 7/1972 | Nerz | 128/214.4 |
| 3,680,562 | 8/1972 | Wittes et al. | 128/347 |
| 3,730,187 | 5/1973 | Reynolds | 128/349 R |
| 3,821,957 | 7/1974 | Riely et al. | 128/348 |
| 3,860,006 | 1/1975 | Patel | 128/347 |
| 3,875,938 | 4/1975 | Mellor | 128/214.4 |
| 3,903,895 | 9/1975 | Alley et al. | 128/350 |
| 3,921,631 | 11/1975 | Thompson | 128/214.4 |
| 3,938,530 | 2/1976 | Santomieri | 128/349 |
| 4,016,879 | 4/1977 | Mellor | 128/214.4 |
| 4,020,835 | 5/1977 | Nordstrom et al. | 128/214.4 |
| 4,046,144 | 9/1977 | McFarlane | 128/214.4 |
| 4,068,659 | 1/1978 | Moorehead | 128/214.4 |
| 4,073,297 | 2/1978 | Kopp | 128/214.4 |
| 4,079,738 | 3/1978 | Dunn et al. | 128/214.4 |
| 4,166,469 | 9/1979 | Littleford | 128/784 |
| 4,306,562 | 12/1981 | Osborne | 128/348 |
| 4,345,606 | 8/1982 | Littleford | 128/214.4 X |
| 4,362,156 | 12/1982 | Feller et al. | 604/165 |

FOREIGN PATENT DOCUMENTS 21446  1/1981  European Pat. Off. .

Primary Examiner—Dalton L. Truluck
Attorney, Agent, or Firm—Paul C. Flattery; John P. Kirby, Jr.; David L. Hitchcock

[57] ABSTRACT

An introducer catheter (22) through which a primary device (38) may be inserted having a slidable sleeve (16), which prevents premature disruption of the peelable catheter tube (14) and which also remains in position on the primary device (38) after the introducer catheter has been peeled apart. Also provided is an assembly (10) for the implantation of a peelable introducer catheter (22) the assembly comprising a needle (12), with an introducer catheter tube (14) telescopically disposed over the needle (12) which is provided with rupture means (20); a slidable sleeve (16) telescopically disposed over the needle and introducer catheter tube, which prevents premature disruption of the peelable catheter tube; and a securing means (26) which prevents rotation of the introducer catheter tube (14) relative to the needle (12) during implantation of the catheter (22) in the patient (40).

24 Claims, 6 Drawing Figures

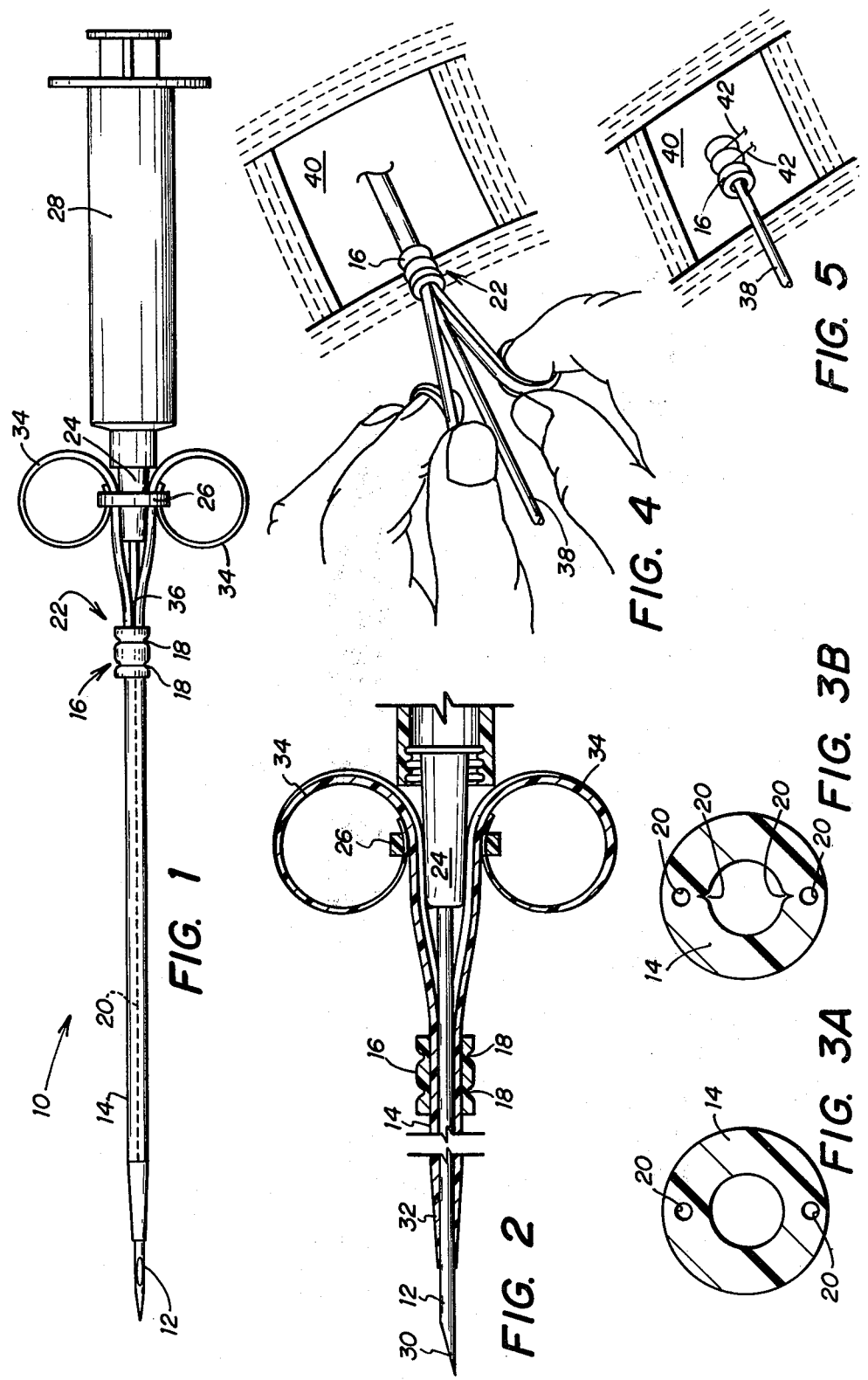

PEELABLE CATHETER WITH SECURING RING AND SUTURE SLEEVE

TECHNICAL FIELD

This invention relates to the medical arts, and in particular, to catheters and catheter assemblies and the securing of such catheters and other implanted devices to the body.

BACKGROUND ART

The use of catheters in the medical field is well known. Catheters are of many different designs depending on the task to be accomplished. For example, the rigid hypodermic needle is widely used for venipuncture for the withdrawal of blood samples or the injection of medicants. Repeated use of such rigid catheters within a short period, such as during hospitalization, is highly traumatic and discomforting to the patient. During hospitalization, it is preferable to place a single catheter in the patient and allow the catheter to remain in place for an extended period.

Placement of a rigid catheter within the patient for an extended period is undesirable because movement of the rigid catheter after implantation causes additional trauma to the patient. When a rigid catheter was implanted for an extended period, the portion of the body in which the rigid catheter was implanted was immobilized to minimize the risk of movement of the rigid catheter relative to the lumen to prevent injury. This practice was uncomfortable and prone to undetected injurious movement when the patient slept.

More recently, it has been the practice to insert a pliant catheter into the vein for an extended period for the periodical administering of fluids, transfusions, medication, collecting blood samples, etc. These flexible catheters are of pliable material and substantially reduce the risk of puncturing the lumen wall in the event of movement relative to the lumen. Two commercial techniques have been used to place the distal end of such flexible catheters within the lumen. They generally may be referred to as the "inside-the-needle" and the "outside-the-needle" techniques. In general, both these methods utilize a rigid catheter, such as a hypodermic needle, for initial penetration of the skin and venipuncture. The "inside-the-needle" technique provides for the insertion of the flexible catheter through the hollow hypodermic needle. Once the flexible catheter is in place, the needle is removed. This technique necessarily requires a small flexible catheter and its attendant disadvantages. Such small catheters are difficult to insert because they easily bend or tear and are difficult to manipulate. Therefore, the implantation of these catheters requires careful manipulation of the needle and catheter which necessitates a relatively long time complete the implantation thereby increasing the risk of injury to the patient.

The "outside-the-needle" technique has the advantages that the catheter may be larger with increased capacity. This technique suffers the disadvantage, however, that the catheter must be rigid enough to penetrate the tissue as it advances to the distal end of a needle. Once the semi-rigid catheter is in place, the needle is then withdrawn from inside the catheter. These semi-rigid catheters suffer the disadvantage that they are more likely to cause additional trauma if they move relative to the lumen. However, the semi-rigid "over-the-needle" catheters, represent an improvement over the rigid metal catheter as they eliminate the sharpened point of the needle.

A third technique has been developed which combines the two prior methods to overcome their disadvantages. This combination technique has two variations.

A first variation of the combination technique involves a multistep procedure. First, a needle is inserted into the vein. A spring wire stylet is introduced into the vein through the needle, after which the needle is removed. A semi-rigid catheter tube and dilator is then placed over the spring wire stylet and guided into position in the vein. Once the semi-rigid catheter is positioned in the patient, the wire stylet and dilator are removed thereby allowing a primary device, such as an infusion catheter, to be inserted therethrough. Once the primary device is in place, the semi-rigid catheter is removed from the patient, and from around the primary device. This method suffers from the disadvantage of requiring a relatively long time for completion, which increases the exposure of the patient to associated injuries.

A second variation of the combined technique is disclosed in co-pending application Ser. No. 259,281 assigned to the assignee of the present invention. This application is entitled "Peelable Catheter Introduction Device". This technique eliminates many of the steps of the previously described combined method. This technique calls for the implantation of an introducer catheter by the "over-the-needle" technique. Once the introducer catheter is in place, the needle is withdrawn leaving a semi-rigid introducer catheter implanted in the patient which is less prone to cause injuries because it is semi-rigid and has a fairly blunt distal end; therefore, it is also less likely to puncture the lumen wall if moved during implantation of the infusion catheter. A pliant infusion catheter is then implanted within the patient through the introducer catheter. Once the pliant infusion catheter is properly placed within the lumen, the introducer catheter is removed from the patient and from around the infusion catheter. In order to facilitate removal of the introducer catheter, the tubes have been mechanically scored to provide weakened lines along which the catheter tube could be ruptured and then peeled apart. This technique permits a larger diameter pliant infusion catheter to be implanted within the patient than is normally possible by the previous "inside-the-needle" technique. Also, this dual technique is less likely to cause additional trauma to the patient, because the semi-rigid inducer catheter with a fairly blunt end is less likely to puncture the lumen wall if moved during implantation of the infusion catheter. In addition, the larger diameter infusion catheter is more easily manipulated and is less likely to fold, bend or tear during implantation. Thus, it may be more quickly implanted thereby reducing the period of time the patient is exposed to the risks associated with implantation.

Introducer catheters of the semi-rigid design have also been utilized to insert diagnostic and therapeutic devices, e.g., pacemaker leads. In some applications, the device inserted through the introducer catheter is to be implanted within the patient for a period of time, and in these applications, a peelable introducer catheter is desirable. As used herein, "primary device" will refer to the device inserted through the introducer catheter whether it is an infusion catheter, a diagnostic or therapeutic device.

The introducer catheters previously used in a dual technique are free to rotate about the stylet or needle presenting a possible source of abrasion to the tissue during implantation. Previous peelable introducer catheters were also rather difficult to remove from about the infusion catheter once it was implanted because the mechanical scoring of the catheter tube could not be consistently reproduced. Thus, a need has arisen to provide an introducer catheter which does not rotate about the needle during the implantation and from which the needle may easily be removed and which is easily removed from the infusion catheter when desired, but is not subject to premature rupture during its implantation or the subsequent implantation of the infusion catheter.

DISCLOSURE OF THE INVENTION

In one respect, the present invention relates to an introducer catheter assembly for the implantation of a primary device. In another respect, the present invention relates to an introducer catheter tube provided with an attachment means for securing the tube to a needle, and further provided with rupture means and grasping means to facilitate removal of the catheter tube from the patient and from about the primary device. In still another aspect, the present invention relates to a slidable suture sleeve to prevent premature rupture of the catheter tube and to provide a means for attaching the primary device to the patient.

In accordance with another aspect of the present invention, an introducer catheter grouping is provided for implanting the introducer catheter within the patient. The grouping comprises an introducer catheter and a needle for venipuncture and for guiding the introducer catheter.

In accordance with another aspect of the present invention, an introducer catheter assembly is provided for implanting the introducer catheter within a patient. The assembly includes a needle for venipuncture and for guiding the introducer catheter. An introducer catheter is telescopically disposed and adhered to the needle to prevent rotation of the catheter tube relative to the needle during implantation.

In accordance with another aspect of the present invention, an introducer catheter is provided for the implantation within a patient and the guiding of an infusion catheter, diagnostic or therapeutic equipment within the patient. The introducer catheter tube is provided with a means to adhere the tube to the needle to prevent both rotational and telescopic movement of the tube relative to the needle during implantation. The introducer catheter tube is further provided with a rupture means and a grasping means to facilitate removal of the tube from the needle and later from around the infusion catheter, therapeutic or diagnostic equipment. Disposed telescopically over the introducer catheter tube is a slidable suture sleeve.

In accordance with yet another aspect of the present invention, a slidable suture sleeve is provided for preventing premature rupture of the introducer catheter during implantation of catheter and introduction of devices therethrough, and for securing the device to the patient. The slidable sleeve is moved from the proximal end of the introducer catheter to the distal end when the catheter is pulled apart. After the introducer catheter has been completely ruptured and removed from about the primary device, the suture sleeve remains disposed over the primary device providing a location for securing the primary device to the patient.

BRIEF DESCRIPTION OF DRAWINGS

A more complete understanding of the invention and its advantages will be apparent from the following Detailed Description taken in conjunction with the accompanying Drawings in which:

FIG. 1 is a side view of the introducer catheter assembly attached to a standard syringe;

FIG. 2 is a cross-sectional view of the introducer catheter assembly taken along the longitudinal axis;

FIGS. 3A and 3B are cross-sectional views of various configurations of the catheter tube;

FIG. 4 is a top elevational view of the introducer catheter tube placed within the patient with an infusion catheter inserted therein and the catheter tube being pulled apart; and FIG. 5 is a top elevational view of the infusion catheter implanted within the patient and secured to the patient by the slidable suture sleeve sutured to the patient.

DETAILED DESCRIPTION

FIG. 1 illustrates the introducer catheter assembly, generally as 10, which comprises a needle 12 and telescopically disposed over needle 12 is introducer catheter tube 14. Disposed telescopically over introducer catheter tube 14 and needle 12 is slidable suture sleeve 16 provided with channels 18. The introducer catheter tube 14 is provided with one or more rupture lines 20, which are longitudinally weakened areas along which the tube may rupture when manually disrupted. The combination of the introducer catheter tube 14 and slidable suture sleeve 18 comprises the introducer catheter 22. Introducer catheter 22 is secured to the needle 12 at hub section 24 by ring 26. Introducer catheter assembly 10 is attached to standard syringe 28.

FIG. 2 is a cross-sectional view of FIG. 1 taken along the longitudinal axis of introducer catheter assembly 22 without the syringe. Needle 12 may be of any design suitable for venipuncture, for example, a standard hypodermic needle. As illustrated, needle 12 is a standard metal hypodermic needle provided with a pointed distal end 30 and hub section 24 suitable for engaging a standard syringe 28 such as illustrated in FIG. 1.

As shown in FIG. 2, introducer catheter tube 14 is telescopically disposed over needle 12. Introducer catheter tube 14 is preferably constructed of semi-rigid polymeric material which is translucent. Translucent material is desirable in order to allow better visibility of the primary device inserted through the introducer catheter 22. Introducer catheter tube 14 is generally of constant diameter, but is preferably beveled at distal end 32 to facilitate penetration of the tissue by the introducer catheter 22. This bevel also serves to blunt distal end 32. It is desirable that end 32 be blunt in order to minimize the risk of injury to the patient by puncture of the lumen walls after it has been implanted. Catheter tube 14 is split apart at the proximal end to provide grasping means, such as loops 34. It will be appreciated that any suitable means by which the operator may firmly grasp the proximal end of the catheter tube 14 is acceptable, for example, tabs instead of loops 34 as illustrated.

Introducer catheter tube 14 is secured to needle 12 by any suitable means which prevents rotation of the catheter tube with respect to the needle during implantation in the patient. In FIG. 2, introducer catheter tube 14 is secured to the needle 12 by ring 26. Ring 26 is preferably a heat shrinkable material and is of sufficient strength to prevent rotation of introducer catheter tube 14 relative to needle 12 during implantation but is weak enough to be easily broken when loops 34 are manually pulled apart. Preferably, ring 26 holds the split ends of catheter tube 14 to the needle hub 24. This location provides an area of increased surface area on the needle which may be engaged by the heat shrinkable ring, thereby, preventing rotation. The ring 26 also helps to eliminate unwanted telescopic movement between the catheter tube 14 and the needle 12, reducing trauma to the patient and keeping the distal end 30 of the needle 12 in spaced relation to the tube 14.

It will be appreciated by one skilled in the art that ring 26 is optional, although preferred. As used herein, "introducer catheter grouping" refers to the introducer catheter assembly 10 without the ring 26. Thus, the introducer catheter grouping comprises the introducer catheter 22 telescopically disposed over the needle 12 (the introducer catheter grouping is not illustrated separately).

Telescopically disposed over the needle 12 and the introducer catheter tube 14 is slidable suture sleeve 16. Slidable sleeve 16 is originally positioned near the proximal end of catheter tube 14 where the tube splits 36 to form the loops 34. In this position the sleeve 16 constrains the catheter tube 14 along the rupture lines 20. As the introducer catheter tube 14 penetrates the tissue, the proximal portion of the tube rests upon the needle hub 24. The sleeve 16 reinforces the tube 14 at the location where it is split 36 and prevents propagation of the split along the rupture lines 20.

FIGS. 3a and 3b are cross-sectional views of the introducer catheter tube 14 showing various configurations of the tube 14 and rupture lines 20. Earlier catheter tubes were provided with rupture lines 20, by mechanically scoring the catheter tube 14. The scoring was unsatisfactory because it created a random series of local strong points which caused disruption of the catheter to be jerky and thus uncomfortable to the patient. It is preferable, to provide rupture lines 20 in the tube during extrusion of the tube. As shown in FIGS. 3A and 3B these rupture lines may be in any desired configuration. The lines thus produced created rupture lines 20 of uniform weakness in the catheter tube 14 and allowing smooth rupture of the catheter tube 14. The rupture lines may also be provided by construction of the introducer catheter tube 14 by orientation of the polymeric material during extrusion, thus allowing the splitting of the material due to the axially alignment from the polymeric structure. It will also be appreciated by those skilled in the art that the rupture means may be provided by a combination of oriented polymeric material and the extrusion of rupture lines which provide a consistently weaker area, or the combination of oriented polymeric material and mechanical scoring.

The needle 12 is used to implant the introducer catheter 22. Once the introducer catheter 22 is implanted within the patient, the tube 14 is grasped at loops 34 and pulled apart with sufficient force to break ring 26. This frees the needle 12 which is then withdrawn from the catheter tube 14. As a result, introducer catheter 22 is implanted within the patient and the beveled blunt distal end 32 of the catheter tube 14 rests in the lumen. After the needle has been withdrawn, the primary device to be introduced into the patient is inserted into the introducer catheter tube 14 of introducer catheter 22. FIG. 4 illustrates a pliant infusion catheter 38 as the primary device being inserted into the introducer catheter tube 14. It will be appreciated by those skilled in the art that other primary devices may be introduced through catheter tube 14, for example, pacemaker leads.

The loops 34 are initially pulled apart with sufficient force to break ring 26 but not to propagate the split along the rupture lines 20. Suture sleeve 16 tends to reinforce the catheter tube preventing accidental rupturing of the tube 14 when the loops 34 are first pulled apart. The sleeve 16 also serves to prevent premature splitting of the catheter tube 14 during insertion of the primary device therethrough, infusion catheter 38.

Once infusion catheter 38 is in place within the patient 40, the loops 34 of tube catheter 14 are grasped and pulled apart, thereby withdrawing catheter tube 14 from the patient 40 and rupturing the tube along the rupture lines 20, in a fashion similar to peeling a banana. The force applied to rupture the tube moves sleeve 16 towards the distal end and eventually off of introducer catheter tube 14. At this point, as shown in FIG. 5, tube catheter 14 is completely ruptured and may be removed from around an infusion catheter 38. Alternatively, the sleeve 16 may be held while the catheter tube 14 is moved axially away from the patient, such that sleeve 16 remains about infusion catheter 38 but no longer remains about the tube 14. The tube 14 may then be completely ruptured and removed from the infusion catheter 38. The slidable sleeve 16 remains and telescopically around the primary device, infusion catheter 38. Sleeve 16 may be used to secure the infusion catheter 38 to the patient 40 by suturing the sleeve 16 to the patient 40. Alternatively, sleeve 16 may be taped or otherwise attached to the patient. For example, sleeve 16 can be designed with tabs carrying an adhesive covered by a protective layer which could be removed to expose the adhesive, the tabs could then be folded down applying the adhesive to the patient and thus securing the suture sleeve to the patient. The sleeve 16 is preferably supplied with channels 18 between which the sutures may rest, and preferably two or more channels 18 are provided so that the sutures 42 may be distributed along the sleeve 16 and thus distributing force along the sleeve 16.

While only one embodiment of the present invention has been described in detail herein and shown in the accompanying drawings, it will be evident that various further modifications are possible without departing from the scope of the invention.

We claim:

1. In a two-step introduction assembly for implanting an introducer catheter within a patient to provide a path for introduction of a primary device, whereby the introducer catheter may be removed and discarded while the primary device remains in operative position, the assembly including a needle for venipuncture and a peelable introducer catheter over the needle having at least one longitudinal rupture means for substantially its entire length along which the catheter may be ruptured, the improvement comprising:

(a) a slidable sleeve snuggly engaging the introducer catheter tube having a proximal end and a distal end and slidably mounted about the proximal end of the catheter to protect the catheter from inadvertent separation along the rutpure means and being slidable to the distal end of said catheter tube under the influence of manual disruption of the catheter tube along the rupture line from the proximal end, whereby the introducer catheter tube may be discarded after disruption along the rupture line while the sleeve remains in position on the primary device as a securing site; and (b) a securing ring snuggly engaging the introducer catheter and needle at the proximal end of the catheter and needle, said ring being affixed to said catheter and needle so as to prevent rotation of the catheter with respect to the needle during implantation and being sufficiently weak that it may be broken under the influence of manually applied pressure.

2. The assembly of claim 1 wherein the slidable sleeve has two or more reduced parameter sections forming channels suitable for engaging sutures.

3. The assembly of claims 1 or 2 in which the proximal end of the introducer is split apart to provide grasping means for the application of force to break said ring and to disrupt said tube.

4. An introducer catheter assembly for the two-step introduction of a primary device into the vascular system by providing an assembly for implantation of the introducer catheter into a patient to provide a path for introduction of the primary device thereby the introducer catheter may be removed and discarded while the primary device remains in operative position, the assembly comprising:

(a) a needle suitable for venipuncture;
(b) an introducer catheter tube having a proximal end and a distal end telescopically disposed over said needle and slidably engaging said needle;
(c) rupture means extending longitudinally substantially the entire length of said introducer catheter to provide an area along which the catheter may be disrupted;
(d) grasping means disposed on the proximal end of said catheter;
(e) a securing means to secure said catheter to said needle so as to prevent rotation of said catheter with respect to said needle during implantation and being breakable to permit withdrawal of the needle from the catheter when desired; and
(f) a slidable sleeve engaging the catheter tube and slidably mounted about the proximal ends of the catheter tube to protect the catheter tube from inadvertently separating along the rupture line, and being slidable under the influence of manual disruption of the catheter tube along the rutpure line, whereby the catheter tube may be discarded after disruption along the rupture line.

5. The assembly of claim 4 wherein said slidable sleeve has two or more channels suitable for receiving sutures therein.

6. An introducer catheter through which a primary device can be inserted into a lumen comprising:

(a) an introducer catheter tube having a proximal end and a distal end;
(b) said introducer catheter tube being constructed of axially oriented polymeric material which is oriented so as to weaken the tube longitudinally thereby facilitating disruption of said tube along substantially its entire length; and
(c) a slidable sleeve telescopically disposed on the outer surface of said introducer catheter tube, said sleeve being slidable towards the distal end by force exerted upon it through said introducer catheter tube as it is disrupted.

7. The introducer catheter of claim 6 wherein said introducer catheter tube has at least one longitudinal mechanical score line for substantially its entire length along which the catheter may be disrupted.

8. The introducer catheter of claim 6 wherein said introducer catheter tube has been extruded to provide at least one longitudinal line of reduced wall thickness for substantially its entire length along which the catheter tube may be disrupted.

9. An introducer catheter through which a primary device can be inserted into a lumen comprising:

(a) an introducer catheter tube;
(b) said introducer catheter tube having a distal end and a proximal end being extruded to provide at least one longitudinal line of reduced wall thickness for substantially its entire length along which the catheter tube may be disrupted; and
(c) a slidable sleeve telescopically disposed on the outer surface of said introducer catheter tube, said sleeve being slidable towards the distal end by force exerted upon it through said introducer catheter tube as it is disrupted.

10. The introducer catheter of claims 6, 7, 8, or 9 wherein said introducer catheter tube is beveled at the distal end such that the smallest outside diameter of said catheter tube is at the extreme distal end of said catheter tube.

11. The introducer catheter of claim 5 wherein said introducer catheter tube is partially split apart at the proximal end to provide tabs by which said introducer catheter tube may be grasped and peeled apart by manual manipulation thereby causing the slidable sleeve to move towards the distal end.

12. The introducer catheter of claims 6, 7, 8 or 9 wherein said introducer catheter tube is partially split apart at the proximal end to provide tabs by which said introducer catheter tube may be grasped and peeled apart by manual manipulation thereby causing the slidable sleeve to move towards the distal end.

13. An introducer catheter grouping comprising:

(a) a hollow needle for venipuncture;
(b) an introducer catheter tube having a proximal end of generally constant diameter disposed telescopically over said needle and extending from the proximal end thereof;
(c) said introducer catheter tube being extruded to provide at least one longitudinal line of reduced wall thickness for substantially its entire length along which said catheter tube may be disrupted; and
(d) a slidable sleeve telescopically disposed over said introducer catheter near the proximal end of said introducer catheter to prevent the premature splitting apart of the introducer catheter tube.

14. An introducer catheter grouping comprising:

(a) a hollow needle for venipuncture;
(b) an introducer catheter tube having a proximal end and a distal end of generally constant diameter disposed telescopically over said needle and extending from the proximal end thereof;
(c) said introducer catheter tube being constructed of axially oriented polymeric material which is oriented so as to weaken the tube longitudinally thereby facilitating disruption of said tube along substantially its entire length; and
(d) a slidable sleeve telescopically disposed over said introducer catheter tube near the proximal end of said introducer catheter tube to prevent the premature disruption of the tube, said sleeve being slidable towards the distal end by force exerted upon it through said introducer catheter tube as it is disrupted.

15. The introducer catheter grouping of claim 14 wherein said introducer catheter tube has at least one longitudinal mechanical score line for substantially its entire length along which the catheter may be disrupted.

16. An introducer catheter grouping comprising:
(a) a hollow needle for venipuncture;
(b) an introducer catheter tube having a proximal end and a distal end of generally constant diameter disposed telescopically over said needle and extending from the proximal end thereof;
(c) said catheter tube being constructed of axially oriented polymeric material which is oriented so as to weaken the tube longitudinally and which has been extruded to provide at least one longitudinal line of reduced wall thickness for substantially its entire length along which the catheter tube may be disrupted; and
(d) a slidable sleeve telescopically disposed over said introducer catheter tube near the proximal end of said introducer catheter tube to prevent the premature disruption of the tube, said sleeve being slidable towards the distal end by force exerted upon it through said introducer catheter tube as it is disrupted.

17. The introducer catheter grouping of claims 13, 14, 15 or 16 wherein said introducer catheter tube is beveled at the distal end such that the smallest outside diameter of said catheter tube is at the extreme distal end of said catheter tube.

18. The introducer catheter of claim 17 wherein said introducer catheter tube is partially split apart at the proximal end to provide tabs by which said introducer catheter may be grasped and peeled apart by manual manipulation thereby causing the slidable sleeve to move towards the distal end.

19. The introducer catheter of claims 13, 14, 15 or 16 wherein said introducer catheter tube is partially split apart at the proximal end to provide tabs by which said introducer catheter tube may be grasped and peeled apart by manual manipulation thereby causing the slidable sleeve to move towards the distal end.

20. In a two-step introduction assembly for implanting an introducer catheter within a patient to provide a path for introduction of a primary device, whereby the introducer catheter may be removed and discarded while the primary device remains in operative position, comprising:
(a) a needle for venipuncture;
(b) an introducer catheter tube having a proximal end and a distal end telescopically disposed over said needle and slidably engaging said needle;
(c) rupture means extending longitudinally substantially the entire length of said introducer catheter to provide an area along which said catheter tube may be disrupted;
(d) securing means to secure said catheter to said needle so as to prevent rotation of said catheter with respect to said needle during implantation and being breakable to permit withdrawal of the needle from the catheter when desired, said securing means comprising a heat shrink band located circumferentially around the proximal end of both said needle and said catheter tube.

21. The introducer catheter assembly of claim 20 wherein said rupture means is at least one longitudinal mechanical score line along substantially the entire length of said introducer catheter tube.

22. The introducer catheter assembly of claim 20 or 21 wherein said introducer catheter tube has grasping means disposed on the distal end thereof.

23. The assembly of claim 20 wherein said introducer catheter tube has been extruded to provide at least one longitudinal line of reduced wall thickness for substantially the entire length along which said catheter tube may be disrupted.

24. The assembly of claim 20 wherein said introducer catheter tube is constructed of axially oriented polymeric material which is oriented so as to weaken the tube longitudinally thereby facilitating disruption of said catheter tube along substantially its entire length.

* * * * *